United States Patent
Klug et al.

(10) Patent No.: US 9,662,287 B2
(45) Date of Patent: *May 30, 2017

(54) PROCESS FOR PREPARING ACYLGLYCINATES AND COMPOSITIONS COMPRISING SUCH COMPOUNDS

(75) Inventors: Peter Klug, Grossostheim (DE); Franz-Xaver Scherl, Burgkirchen (DE)

(73) Assignee: Clariant International Ltd., Muttenz (CH)

( * ) Notice: Subject to any disclaimer, the term of this patent is extended or adjusted under 35 U.S.C. 154(b) by 387 days.

This patent is subject to a terminal disclaimer.

(21) Appl. No.: 14/232,844

(22) PCT Filed: Jul. 11, 2012

(86) PCT No.: PCT/EP2012/002931
§ 371 (c)(1),
(2), (4) Date: Apr. 1, 2014

(87) PCT Pub. No.: WO2013/010650
PCT Pub. Date: Jan. 24, 2013

(65) Prior Publication Data
US 2014/0213665 A1   Jul. 31, 2014

(30) Foreign Application Priority Data
Jul. 15, 2011   (DE) .................. 10 2011 107 503

(51) Int. Cl.
| A61K 8/42 | (2006.01) |
| C07C 233/47 | (2006.01) |
| A61Q 19/00 | (2006.01) |
| C07C 233/49 | (2006.01) |
| A61Q 19/10 | (2006.01) |
| A61K 8/04 | (2006.01) |
| A61K 8/44 | (2006.01) |
| C07C 231/02 | (2006.01) |

(52) U.S. Cl.
CPC ............... *A61K 8/42* (2013.01); *A61K 8/046* (2013.01); *A61K 8/44* (2013.01); *A61Q 19/00* (2013.01); *A61Q 19/10* (2013.01); *C07C 231/02* (2013.01); *C07C 233/47* (2013.01); *C07C 233/49* (2013.01); *A61K 2800/10* (2013.01)

(58) Field of Classification Search
None
See application file for complete search history.

(56) References Cited

U.S. PATENT DOCUMENTS

2010/0273879 A1 * 10/2010 Klug .................. A61K 8/44
514/554

FOREIGN PATENT DOCUMENTS

WO   WO2009065530   * 5/2009

* cited by examiner

*Primary Examiner* — Matthew Coughlin
*Assistant Examiner* — Po-Chih Chen
(74) *Attorney, Agent, or Firm* — Tod A. Waldrop

(57) ABSTRACT

A process for preparing acylglycinates of the formula (I) wherein $R^1$ is a linear or branched, saturated alkanoyl group having 6 to 30 carbon atoms, or is a linear or branched, singly or multiply unsaturated alkenoyl group having 6 to 30 carbon atoms, and $Q^+$ is a cation, wherein glycine is reacted with fatty acid chloride $R^1Cl$, in water and in the presence of a basic alkali metal compound which yields cations $Q^+$, but in the absence of organic solvents, at 25-50° C. Also described are compositions comprising acylglycinates of the formula (I).

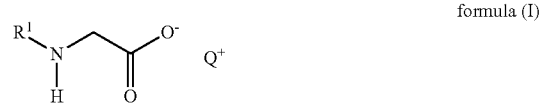

formula (I)

9 Claims, No Drawings

PROCESS FOR PREPARING ACYLGLYCINATES AND COMPOSITIONS COMPRISING SUCH COMPOUNDS

The invention relates to a process for preparing acylglycinates, to compositions comprising acylglycinates, and to the use thereof for production of cosmetic formulations or as a surfactant in cosmetic formulations.

Acylglycinates, for example cocoylglycinates with $Na^+$ or $K^+$ as counterions, are surfactants which are particularly valued in cosmetics for face-cleansing formulations in Asia in skin-cleansing products. The surfactants, especially sodium and potassium cocoylglycinate, give excellent foaming in slightly alkaline solution and give rise to a pleasant, non-oily skinfeel.

In contrast to the corresponding N-methylglycine derivatives, known as the sarcosinates, glycinates, however, have problematic properties in the course of preparation. As described in JP 8053693 (Ajinomoto), acylglycinates can be obtained in water without additional solvents in purities of just over 90%, but form very high-viscosity reaction solutions in the Schotten-Baumann reaction. JP 8053693 proposes the addition of alcohols such as isopropanol, isobutanol or tert-butanol in the course of preparation of acylglycinates.

However, this course of action is not advantageous because of the odor of the alcohols, for which reason the alcohols also have to be removed again from the reaction mixture after acidification and phase separation, and the desired alkanoylglycinate is usually obtained in low-salt quality after neutralization. This process is costly and inconvenient and results in sodium chloride-containing wastewater which has to be disposed of.

WO 2009/065530 (Clariant) describes a method for producing acylglycinates of the formula $R^1$—NH—$CH_2COO^-$ $X^+$ in which $R^1$ is a linear or branched, saturated alkanoyl group having 6 to 30 carbon atoms or is a linear or branched, mono- or polyunsaturated alkenoyl group having 6 to 30 carbon atoms, and $Q^+$ is a cation selected from the alkali metal $Li^+$, $Na^+$ and $K^+$, wherein glycine is reacted with fatty acid chloride $R^1Cl$ in water and in the presence of a basic alkali metal compound which provides cations $Q^+$ selected from $Li^+$, $Na^+$ and $K^+$, but in the absence of organic solvents, at 30 to 35° C., and the proportion of fatty acid chloride $R^1Cl$ containing acyl groups $R^1$ having 18 or more carbon atoms, based on the total amount of fatty acid chloride used, is less than 2.0% by weight. In addition, WO 2009/065530 also describes particular compositions comprising specific acylglycinates and water but no organic solvents, and the use thereof for production of cosmetic formulations or as a surfactant in cosmetic formulations. However, a disadvantage of the method described in WO 2009/065530 is that no inexpensive standard fatty acid chain cuts are used, and therefore possible economic improvements still exist. Moreover, the foaming characteristics of the resulting surfactants or compositions is still in need of further improvement, more particularly the total foam heights achievable.

WO 02/057217 (Cognis) discloses a process for preparing acylamino acids, in which a reactor is initially charged with a mixture of at least one amino acid or salt thereof and an alkali metal source, and this is admixed in a mixing element with fatty acid halides of the formula $R^1COX$ in which $R^1$ is an alkyl or alkenyl radical having 6 to 22 carbon atoms and X is chlorine, bromine, iodine, the products resulting therefrom, and the use thereof in cosmetic products and in washing, rinsing and cleaning compositions. In the examples according to the teaching of WO 02/057217, the preparation is performed in the presence of organic solvents.

The problem addressed was therefore that of providing a process for preparing acyl-glycinates or compositions comprising acyl glycinates, which does not have the above-mentioned disadvantages or at least mitigates these disadvantages, and especially has the advantage that it can be effected without employing organic solvents, using chain cuts of the fatty acid component which are inexpensive and available on the market, and gives acylglycinates of high purity and having advantageous foaming capacity, for example advantageous achievable total foam heights. The process should also enable the direct production of compositions having a high active content of acylglycinate and having low viscosities.

A further problem addressed was also that of providing corresponding compositions comprising acylglycinates. These compositions should therefore have, for example, the following advantages: they should contain the acylglycinate in high purity, have advantageous foaming capacity and especially enable advantageous achievable total foam heights. The compositions should have low viscosities and, at the same time, contain the acylglycinate with high active content. In addition, they should not contain any organic solvents. It should also be possible to produce the acylglycinates present in the compositions or the compositions themselves with chain cuts of the fatty acid component which are inexpensive and available on the market.

It has been found that, surprisingly, the problem is solved when acylglycinates of the formula (I)

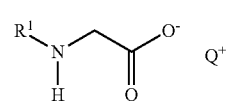

formula (I)

in which
$R^1$ is a linear or branched, saturated alkanoyl group having 6 to 30, preferably 8 to 22 and more preferably 8 to 18 carbon atoms, or a linear or branched, mono- or polyunsaturated alkenoyl group having 6 to 30, preferably 8 to 22 and more preferably 8 to 18 carbon atoms, and
$Q^+$ is a cation selected from the alkali metal cations $Na^+$ and $K^+$ and is preferably $Na^+$,
are prepared by reacting glycine with fatty acid chloride $R^1Cl$ where $R^1$ is as defined in formula (I), in water and in the presence of a basic alkali metal compound which provides cations $Q^+$ selected from $Na^+$ and $K^+$ and preferably $Na^+$, but in the absence of organic solvents, at a temperature of 25-50° C., preferably at a temperature of 30-40° C., and the proportion of fatty acid chloride $R^1Cl$ containing unsaturated acyl groups $R^1$ having 18 carbon atoms, based on the total amount of fatty acid chloride used, is greater than or equal to 2.0% by weight and, at the same time, the proportion of fatty acid chloride $R^1Cl$ containing saturated acyl groups $R^1$ having 8 and 10 carbon atoms, based on the total amount of fatty acid chloride used, is greater than or equal to 3.0% by weight in each case.

The invention therefore provides a process for preparing acylglycinates of the formula (I)

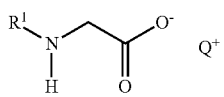

formula (I)

in which
R¹ is a linear or branched, saturated alkanoyl group having 6 to 30, preferably 8 to 22 and more preferably 8 to 18 carbon atoms, or a linear or branched, mono- or polyunsaturated alkenoyl group having 6 to 30, preferably 8 to 22 and more preferably 8 to 18 carbon atoms, and
Q⁺ is a cation selected from the alkali metal cations Na⁺ and K⁺ and is preferably Na⁺,
wherein glycine is reacted with fatty acid chloride R¹Cl where R¹ is as defined in formula (I), in water and in the presence of a basic alkali metal compound which provides cations Q⁺ selected from Na⁺ and K⁺ and preferably Na⁺, but in the absence of organic solvents, at 25-50° C., preferably at 30-40° C., and the proportion of fatty acid chloride R¹Cl containing unsaturated acyl groups R¹ having 18 carbon atoms, based on the total amount of fatty acid chloride used, is greater than or equal to 2.0% by weight and, at the same time, the proportion of fatty acid chloride containing saturated acyl groups R¹ having 8 and 10 carbon atoms, based on the total amount of fatty acid chloride used, is greater than or equal to 3.0% by weight in each case.

In the context of the present invention, the linear or branched, saturated alkanoyl groups R¹ from formula (I) and the linear or branched, mono- or polyunsaturated alkenoyl groups R¹ from formula (I) are also referred to collectively as "acyl groups".

The process according to the invention gives compositions which are in the form of monophasic compositions at 40° C. and are therefore suitable for economic transport.

The fatty acid chlorides used in the process according to the invention can be obtained by methods known to those skilled in the art, for example by chlorinating fatty acids, for example commercial coconut fatty acid, by means of phosphorus trichloride, thionyl chloride or phosgene.

The basic alkali metal compounds are preferably carbonates or hydroxides of the alkali metal cations Na⁺ or K⁺, i.e. $Na_2CO_3$, NaOH, $K_2CO_3$ or KOH, or mixtures thereof. Particular preference is given to $Na_2CO_3$ or NaOH or mixtures thereof, and NaOH is especially preferred.

The process according to the invention is preferably performed at a pH of 9 to 13, more preferably 12 to 13.

Additionally preferably, the process according to the invention is performed in such a way that glycine and fatty acid chloride R¹Cl are used in approximately equimolar amounts. More preferably, the fatty acid chloride R¹Cl, based on glycine, is used in an equimolar amount or in a slight deficiency. The molar ratio of glycine to fatty acid chloride R¹Cl is especially preferably from 1.1:1.0 to 1.0:1.0 and exceptionally preferably from 1.05:1.0 to 1.0:1.0.

Additionally preferably, in the process according to the invention,
fatty acid chlorides R¹Cl in which R¹ is an acyl group having 6 to 30, preferably 8 to 22 and more preferably 8 to 18 carbon atoms, where
the proportion of fatty acid chlorides having saturated $C_8$ acyl groups is greater than or equal to 3.0% by weight, preferably 3.0-10.0% by weight and more preferably 5.0-8.0% by weight, the proportion of fatty acid chlorides having saturated $C_{10}$ acyl groups is greater than or equal to 3.0% by weight, preferably 3.0-10.0% by weight and more preferably 5.0-8.0% by weight, the proportion of fatty acid chlorides having $C_{12}$ acyl groups is 40.0-55.0% by weight and preferably 44.0-50.0% by weight, the proportion of fatty acid chlorides having $C_{14}$ acyl groups is 13.0-22.0% by weight and preferably 14.0-20.0% by weight, the proportion of fatty acid chlorides having $C_{16}$ acyl groups is 5.0-11.0% by weight and preferably 8.0-10.0% by weight, the proportion of fatty acid chlorides having saturated $C_{18}$ acyl groups is 0-5.0% by weight, preferably 0.1 to 5.0% by weight and more preferably 1.0-3.0% by weight, and the proportion of fatty acid chlorides having unsaturated $C_{18}$ acyl groups, preferably oleyl chloride, is greater than or equal to 2.0% by weight, preferably 2.0-11.0% by weight and more preferably 4.0-10.0% by weight, based in each case on the total amount of fatty acid chloride used, are reacted. Preferably, this reaction takes place in the presence of a basic alkali metal compound which provides Na⁺ cations. The basic alkali metal compounds are preferably $Na_2CO_3$ or NaOH or mixtures thereof and more preferably NaOH.

The fatty acid chlorides are preferably linear.

The fatty acid chlorides having 12, 14 and 16 carbon atoms are preferably saturated.

Preferably, the proportion of fatty acid chloride having 8 to 18 carbon atoms, based on the total amount of fatty acid chloride used, is 95% by weight or greater and more preferably 96.5% by weight or greater.

Additionally preferably, in the process according to the invention, cocoyl chlorides are reacted, the cocoyl cut corresponding to a natural coconut fatty acid.

The process according to the invention is preferably executed in such a way that glycine is initially charged in water in the presence of the basic alkali metal compound and the fatty acid chloride is added at 25 to 50° C. and preferably at 30 to 40° C. The fatty acid chloride is preferably added gradually while stirring.

Through the process according to the invention, it is possible to prepare highly concentrated, salt-containing glycinate solutions having a low content of by-products (for example fatty acid salt), which are monophasic and of low viscosity at 40° C. and correspondingly easy to handle, and are additionally cost-effective, since there is no need to conduct any separation step. Moreover, no organic reaction solvent is required, which has to be removed again and possibly disposed of.

The invention therefore further provides compositions comprising
a) one or more acylglycinates of the formula (I)

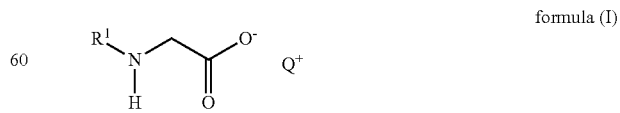

formula (I)

in which
R¹ is a linear or branched, saturated alkanoyl group having 6 to 30, preferably 8 to 22 and more preferably 8 to 18 carbon atoms, or a linear or branched, mono- or polyunsaturated alkenoyl group having 6 to 30, preferably 8 to 22 and more preferably 8 to 18 carbon atoms, and $Q^+$ is a cation selected from the alkali metal cations $Na^+$ and $K^+$ and is preferably $Na^+$, in amounts of 21.0-28.0% by weight and preferably in amounts of 23.0-27.0% by weight, based on the overall composition, and where the proportion of unsaturated acyl groups $R^1$ having 18 carbon atoms in the one or more acylglycinates of the formula (I), based on the total amount of the acyl groups present in the one or more acylglycinates, is greater than or equal to 2.0% by weight and, at the same time, the proportion of saturated acyl groups $R^1$ having 8 and 10 carbon atoms, based on the total amount of the acyl groups present in the one or more acylglycinates, is greater than or equal to 3.0% by weight in each case, and where the proportions mentioned are calculated not on the basis of the acyl groups themselves but on the basis of the fatty acid chlorides corresponding to the acyl groups, b) one or more substances $Q^+Cl^-$ in which $Q^+$ is as defined for $Q^+$ in formula (I), in amounts greater than or equal to 1.0% by weight, preferably in amounts of 1.0 to 8.0% by weight, more preferably in amounts of 2.0 to 7.0% by vveight and especially preferably in amounts of 4.0 to 6.0% by weight, based on the overall composition, c) one or more fatty acid salts of the formula (II)

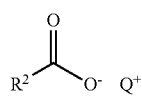

formula (II)

in which $R^2CO$ is as defined for $R^1$ in formula (I) and $Q^+$ is as defined for $Q^+$ in formula (I), in amounts less than or equal to 3.0% by weight, preferably in amounts of 0.01 to 2.0% by weight, more preferably in amounts of 0.1 to 2.0% by weight and especially preferably in amounts of 0.1 to 1.5% by weight, based on the overall composition, and d) water, e) but no organic solvents.

The inventive compositions enable advantageous achievable total foam heights and additionally good foam stabilities.

In a preferred embodiment of the invention, the inventive compositions comprise, as component a), one or more acylglycinates of the formula (I) in which $R^1$ is an acyl group having 6 to 30, preferably 8 to 22 and more preferably 8 to 18 carbon atoms, and $Q^+$ is a cation selected from $Na^+$ and $K^+$, and preferably $Na^+$, in amounts of 21.0-28.0% by weight and preferably in amounts of 23.0-27.0% by weight, based on the overall composition, and where, in the one or more acylglycinates of the formula (I), the proportion of saturated $C_8$ acyl groups is greater than or equal to 3.0% by weight, preferably 3.0-10.0% by weight and more preferably 5.0-8.0% by weight, the proportion of saturated $C_{10}$ acyl groups is greater than or equal to 3.0% by weight, preferably 3.0-10.0% by weight and more preferably 5.0-8.0% by weight, the proportion of $C_{12}$ acyl groups is 40.0-55.0% by weight and preferably 44.0-50.0% by weight, the proportion of $C_{14}$ acyl groups is 13.0-22.0% by weight and preferably 14.0-20.0% by weight, the proportion of $C_{16}$ acyl groups is 5.0-11.0% by weight and preferably 8.0-10.0% by weight, the proportion of saturated $C_{18}$ acyl groups is 0-5.0% by weight, preferably 0.1 to 5.0% by weight and more preferably 1.0-3.2% by weight and the proportion of unsaturated $C_{18}$ acyl groups, preferably of acyl groups derived from oleic acid, is greater than or equal to 2.0% by weight, preferably 2.0-11.0% by weight and more preferably 4.0-10.0% by weight, and where the proportions mentioned are based on the total amount of acyl groups present in the one or more acylglycinates, but are calculated not on the basis of the acyl groups themselves but on the basis of the fatty acid chlorides corresponding to the acyl groups.

The acyl groups in the one or more acylglycinates of the formula (I) are preferably linear.

In the one or more acylglycinates of the formula (I), the acyl groups having 12, 14 and 16 carbon atoms are preferably saturated.

Preferably, the proportion of acyl groups having 8 to 18 carbon atoms in the one or more acylglycinates of the formula (I) is 95% by weight or greater and more preferably 96.5% by weight or greater, where the proportions mentioned are based on the total amount of the acyl groups present in the one or more acylglycinates, but are calculated not on the basis of the acyl groups themselves but on the basis of the fatty acid chlorides corresponding to the acyl groups.

Preference is further given to compositions comprising sodium cocoylglycinate, the cocoyl cut corresponding to a natural coconut fatty acid.

$Q^+Cl^-$ is also referred to in the context of the present application as QCl, e.g. $Na^+Cl^-$ as NaCl.

In the compounds of the formulae (I) and (II) and in $Q^+Cl^-$, $Q^+$ is selected from $Na^+$ and $K^+$, and $Q^+$ is preferably $Na^+$.

The inventive compositions comprise the one or more substances $Q^+Cl^-$ in amounts greater than or equal to 1.0% by weight, preferably in amounts of 1.0 to 8.0% by weight, more preferably in amounts of 2.0 to 7.0% by weight and especially preferably in amounts of 4.0 to 6.0% by weight, based on the overall composition. This is very advantageous, for example, for cosmetic applications because it is possible to dispense with a separate addition of $Q^+Cl^-$ as a viscosity regulator in the final cosmetic formulations produced with the aid of inventive compositions.

The inventive compositions can thus be used advantageously, for example, for cosmetic applications and for production of cosmetic formulations.

The inventive compositions comprise the one or more fatty acid salt(s) of the formula (II) in amounts less than or equal to 3.0% by weight, preferably in amounts of 0.01 to 2.0% by weight, more preferably in amounts of 0.1 to 2.0% by weight and especially preferably in amounts of 0.1 to 1.5% by weight, based on the overall composition.

It is a further advantage of the inventive compositions that they comprise only small amounts of fatty acid salt of the formula (II) and hence comprise acylglycinates of the formula (I) with high purity.

Preferably, the purity of the acylglycinates of the formula (I) and preferably of the sodium cocoylglycinates present in the inventive compositions is 90% or greater and preferably 92% or greater. This purity is based on the sum total of fatty acid salt of the formula (II) and acylglycinate of the formula (I). It is calculated by the formula "purity of the acylglycinates=[amount of acylglycinate:(amount of acylglycinate+ amount of fatty acid salt)]".

The inventive compositions are liquid and monophasic at 40° C.

Also very advantageous is the relatively low viscosity and hence simple handling of the inventive compositions.

Preferably, the inventive compositions have viscosities at 40° C. of less than 5000 mPa·s, more preferably of 50 to 2000 mPa·s and especially preferably of 80 to 500 mPa·s.

The instrument used for the determination of the viscosity is a rotameter from Thermo Haake (Viskotester 550). The spindle used was MV-DIN (45.3 revolutions/minute).

The inventive compositions do not comprise any organic solvents, for example lower alcohols, diols or other organic solvents.

In a particularly preferred embodiment of the invention, the inventive compositions consist of components a), b), c) and d).

In a further particularly preferred embodiment of the invention, the inventive compositions consist of components a), b), c), d) and $H_2NCH_2COO^-Q^+$ where $Q^+$ is a cation selected from $Na^+$ and $K^+$ and is preferably $Na^+$. In these inventive compositions, the compound $H_2NCH_2COO^-Q^+$, based on the overall inventive composition, is present preferably from 0.01 to 2.0% by weight and more preferably from 0.05 to 1.5% by weight.

The invention also further relates to the preparation of the inventive compositions by the process according to the invention.

As already mentioned, the inventive compositions are advantageously suitable for production of cosmetic formulations.

The invention therefore further relates to the use of the inventive compositions for production of a cosmetic formulation. It is particularly advantageous in this context that the inventive compositions can be used as obtained from the process according to the invention, i.e. without further workup or purification.

The inventive compositions are additionally advantageously suitable as surfactants in cosmetic formulations.

The invention therefore further relates to the use of the inventive compositions as surfactants in cosmetic formulations. In this case, the inventive compositions can also be used directly as obtained from the process according to the invention.

The examples and applications which follow are intended to illustrate the invention in detail, without restricting it thereto. All percentages are percent by weight (% by weight) unless explicitly stated otherwise.

COMPARATIVE EXAMPLE 1

Cocoyl Chloride (A): Coconut Cut with Reduced $C_{16}$ and $C_{18}$ Component

Specification of the cocoyl chloride used:
$C_8/C_{10}$ saturated: 10.0-14.0% by weight
$C_{12}$: 60.0-62.0% by weight
$C_{14}$: 19.0-24.0% by weight
$C_{16}$: 3.0-10.0% by weight
$C_{18}$ saturated: <2.0% by weight 37.8 g (0.504 mol) of glycine are dissolved in 276 g of demineralized water while stirring, and the pH (tel quel) is set to 12-13 with sodium hydroxide solution (33% by weight in water). Subsequently, the mixture is heated to 30-35° C. while stirring and 106.4 g (0.478 mol) of cocoyl chloride (A) are metered in at 30-35° C. while cooling the reaction mixture within 6 hours. The pH is kept at 12-13 by simultaneous metered addition of sodium hydroxide solution (33% by weight in water). Toward the end of the metered addition of the cocoyl chloride, the pH is allowed to drop to 9.5-10.5. To complete the reaction, the mixture is stirred at pH 9.5-10.5 for another 2 hours.

The product obtained has the following properties:
at 25° C.: liquid, opalescent
dry residue (1 hour, 140° C.): 31.0% by weight
glycine salt (HPLC): 0.6% by weight
fatty acid salt (HPLC): 0.6% by weight
NaCl (titration): 5.3% by weight
active content: 24.5% by weight
viscosity (35° C.): 756 mPa·s The weight of acylglycinate in the compositions is calculated by the formula "weight of acylglycinate=dry residue−fatty acid salt−glycine salt−$Q^+Cl^-$". The value is referred to as "active content" in the context of the present application.

Comparative example 1 corresponds to the prior art of WO 2009/065530. This affords a solution, liquid at room temperature (25° C.), of sodium cocoylglycinate, but this is based on a chain cut of lower commercial availability.

COMPARATIVE EXAMPLE 2

Coconut Cut with Increased $C_{16/18}$ Component but without $C_8$ and $C_{10}$ Component Distribution of the cocoyl chloride used (B):
$C_{12}$: 55.6% by weight
$C_{14}$: 23.0% by weight
$C_{15}$: 11.1% by weight
$C_{18}$ saturated: 10.3% by weight 36.0 g (0.480 mol) of glycine are dissolved in 280 g of demineralized water while stirring, and the pH (tel quel) is set to 12-13 with sodium hydroxide solution (33% by weight in water). Subsequently, the mixture is heated to 30-35° C. while stirring and 109.6 g (0.456 mol) of cocoyl chloride (B) are metered in at 30-35° C. while cooing the reaction mixture within 6 hours. The pH is kept at 12-13 by simultaneous metered addition of sodium hydroxide solution (33% by weight in water). In the course of the metered addition of the cocoyl chloride, the mixture becomes ever more viscous until it is no longer stirrable. Through addition of 110 g of water and a subsequent increase in the reaction temperature to 40° C., the reaction mixture remains stirrable to a certain degree. Toward the end of the metered addition of the cocoyl chloride, the pH is allowed to drop to 9.5-10.5. To complete the reaction, the mixture is stirred at pH 9.5-10.5 for another 2 hours.

The product obtained has the following properties:
at 25° C.: liquid, cloudy
dry residue (1 hour, 140° C.): 25.8% by weight
glycine salt (HPLC): 0.8% by weight
fatty acid salt (HPLC): 1.2% by weight
NaCl (titration): 4.1% by weight
active content: 19.7% by weight
viscosity: not determined Comparative example 2 shows that higher contents of saturated $C_{16/18}$ fatty acid chlorides lead to glycinate solutions which are of low concentration and cannot be handled if no $C_8$, $C_{10}$ and unsaturated $C_{18}$ acid chloride components are present in the acid chloride.

EXAMPLE 1

Coconut Cut with $C_8$ and $C_{10}$ Components and Unsaturated $C_{18}$ Components Distribution of the cocoyl chloride used:

| Fatty acid chloride | % by weight |
| --- | --- |
| $C_6$ fatty acid chloride | 0.5 |
| $C_8$ fatty acid chloride, saturated | 7.4 |
| $C_{10}$ fatty acid chloride, saturated | 5.9 |
| $C_{12}$ fatty acid chloride | 49.4 |
| $C_{14}$ fatty acid chloride | 18.5 |
| $C_{16}$ fatty acid chloride | 8.4 |
| $C_{18}$ fatty acid chloride, unsaturated | 5.2 |
| $C_{18}$ fatty acid chloride, saturated | 2.2 |
| Sum total x | 2.5 | x: indeterminate substances 18.9 g (0.252 mol) of glycine are dissolved in 146 g of demineralized water while stirring, and the pH (tel quel) is set to 12-13 with sodium hydroxide solution (33% by weight in water). Subsequently, the mixture is heated to 35-40° C. while stirring and 53.1 g (0.239 mol) of cocoyl chloride are metered in at 35-40° C. while cooling the reaction mixture within 6 hours. The pH is kept at 12-13 by simultaneous metered addition of sodium hydroxide solution (33% by weight in water). Toward the end of the metered addition of the cocoyl chloride, the pH is allowed to drop to 9.5-10.5. To complete the reaction, the mixture is stirred at 40° C. and pH 9.5-10.5 for another 2 hours.

The product obtained has the following properties:
at 40° C.: mobile, clear, homogeneous
dry residue (1 hour, 140° C.): 30.0% by weight
glycine salt (HPLC): 0.9% by weight
fatty acid salt (HPLC): 1.8% by weight
NaCl (titration): 5.0% by weight
active content: 22.3% by weight
viscosity (40° C.): 100 mPa·s Inventive example 1 shows that homogeneous glycinate solutions having a high active content are obtained with fatty acid chlorides comprising both significant amounts of $C_8$ and $C_{10}$ fatty acid chloride and unsaturated $C_{18}$ fatty acid chloride (chain cut corresponding to a naturally occurring coconut fatty acid cut).

COMPARATIVE EXAMPLE 3

Coconut Cut with Unsaturated $C_{18}$ Components but Small $C_8$ and $C_{10}$ Components Distribution of the cocoyl chloride used:

| Fatty acid chloride | % by weight |
| --- | --- |
| $C_8$ fatty acid chloride, saturated | 0.1 |
| $C_{10}$ fatty acid chloride, saturated | 0.5 |
| $C_{12}$ fatty acid chloride | 55.1 |
| $C_{14}$ fatty acid chloride | 23.0 |
| $C_{16}$ fatty acid chloride | 10.7 |
| $C_{18}$ fatty acid chloride, unsaturated | 6.8 |
| $C_{18}$ fatty acid chloride, saturated | 2.9 |
| Sum total x | 1.0 | x: indeterminate substances 18.9 g (0.252 mol) of glycine are dissolved in 155 g of demineralized water while stirring, and the pH (tel quel) is set to 12-13 with sodium hydroxide solution (33% by weight in water). Subsequently, the mixture is heated to 35-40° C. while stirring and 57.2 g (0.239 mol) of cocoyl chloride are metered in at 35-40° C. while cooling the reaction mixture within 6 hours. The pH is kept at 12-13 by simultaneous metered addition of sodium hydroxide solution (33% by weight in water). In the course of the metered addition of the cocoyl chloride, the mixture becomes ever more viscous until it is ultimately no longer stirrable. This makes it necessary to raise the temperature first to 45° C. and then to 50° C. In spite of this, the mixture remains viscous. Toward the end of the metered addition of the cocoyl chloride, the pH is allowed to drop to 9.5-10.5. To complete the reaction, the mixture is stirred at 50° C. and pH 9.5-10.5 for another 2 hours.

The product obtained has the following properties:
at 40° C.: unstirrable viscous material
dry residue (1 hour, 140° C.): 31.2% by weight
glycine salt (HPLC): 2.5% by weight
fatty acid salt (HPLC): 4.4% by weight
NaCl (titration): 4.6% by weight
active content: 19.7% by weight
viscosity: not determined Comparative example 3 shows that only unstirrable viscous materials having low purity are obtained as products at 40° C. with fatty acid chlorides comprising no significant amounts of $C_8$ and $C_{10}$ fatty acid chloride but comprising significant amounts of unsaturated $C_{18}$ fatty acid chloride (corresponding to a commercial, naturally occurring coconut fatty acid cut which has been capped).

EXAMPLE 2

Coconut cut with unsaturated components from comparative example 3, supplemented with $C_8$ and $C_{10}$
Distribution of the cocoyl chloride used:

| Fatty acid chloride | % by weight |
| --- | --- |
| $C_8$ fatty acid chloride, saturated | 5.0 |
| $C_{10}$ fatty acid chloride, saturated | 8.0 |
| $C_{12}$ fatty acid chloride | 48.3 |
| $C_{14}$ fatty acid chloride | 20.1 |
| $C_{16}$ fatty acid chloride | 9.3 |
| $C_{18}$ fatty acid chloride, unsaturated | 5.8 |
| $C_{18}$ fatty acid chloride, saturated | 2.5 |
| Sum total x | 1.0 | x: indeterminate substances 18.9 g (0.252 mol) of glycine are dissolved in 156 g of demineralized water while stirring, and the pH (tel quel) is set to 12-13 with sodium hydroxide solution (33% by weight in water). Subsequently, the mixture is heated to 35-40° C. while stirring and 55.5 g (0.239 mol) of cocoyl chloride are metered in at 35-40° C. while cooling the reaction mixture within 6 hours. The pH is kept at 12-13 by simultaneous metered addition of sodium hydroxide, solution (33% by weight in water). The mixture has good stirrability. Toward the end of the metered addition of the cocoyl chloride, the pH is allowed to drop to 9.5-10.5. To complete the reaction, the mixture is stirred at 40° C. and pH 9.5-10.5 for another 2 hours.

The product obtained has the following properties:
at 40° C.: mobile, clear, homogeneous
dry residue (1 hour, 140° C.): 29.7% by weight glycine salt (HPLC): 0.8% by weight
fatty acid salt (HPLC): 1.9% by weight
NaCl (titration): 4.6% by weight
active content: 22.4% by weight
viscosity (40° C.): 388 mPa·s Inventive example 2 shows that glycinate solutions which are homogeneous at 40° C. and have a high active content are obtained with fatty acid chlorides comprising significant amounts both of $C_8$ and $C_{10}$ fatty acid chloride and of unsaturated $C_{18}$ fatty acid chloride (chain cut corresponding to a naturally occurring coconut fatty acid cut).

COMPARATIVE EXAMPLE A

Foaming capacity of the inventive compositions:

The foaming capacity was measured in an SITA foam tester at a surfactant concentration of 0.01% by weight at pH=9 and 37° C. Table 1 below collates the foam heights as a function of the stirring cycles.

TABLE 1

Foam heights measured [mm] as a function of the stirring cycles

| | Stirring cycles | | | | | | | | |
|---|---|---|---|---|---|---|---|---|---|
| | 2 | 4 | 6 | 8 | 10 | 15 | 20 | 25 | 30 |
| Foam heights [mm] Example 1 | 22 | 60 | 98 | 130 | 150 | 195 | 225 | 235 | 245 |
| Foam heights [mm] Comparative example 1 | 96 | 130 | 130 | 130 | 130 | 130 | 130 | 130 | 130 |

The experimental results collated in table 1 show that the inventive acylglycinate enables, or the inventive compositions enable, much higher achievable total foam heights than the acylglycinate or the composition from comparative example 1. The high achievable total foam heights lead, in cosmetic formulations for example, to creamy foams which are sensorily appealing.

The invention claimed is:
1. A composition comprising
a) at least one acylglycinate of the formula (I)

formula (I)

in which
$R^1$ is a linear or branched, saturated alkanoyl group having 6 to 30 carbon atoms, or a linear or branched, mono- or polyunsaturated alkenoyl group having 6 to 30 carbon atoms, and
$Q^+$ is a cation selected from the group consisting of the alkali metal cations $Na^+$ and $K^+$,
in amounts of 21.0-28.0% by weight, based on the overall composition,
and where, in the at least one acylglycinate of the formula (I), the proportion of saturated $C_8$ acyl groups is 5.0-8.0% by weight,
the proportion of saturated $C_{10}$ acyl groups is 5.0-8.0% by weight,
the proportion of $C_{12}$ acyl groups is 44.0-50.0% by weight,
the proportion of $C_{14}$ acyl groups is 14.0-20.0% by weight,
the proportion of $C_{16}$ acyl groups is 8.0-10.0% by weight,
the proportion of saturated $C_{18}$ acyl groups is 1.0-3.0% by weight and
the proportion of unsaturated $C_{18}$ acyl groups is 4.0-10.0% by weight,
and where the proportions are based on the total amount of acyl groups present in the at least one acylglycinate, but are calculated not on the basis of the acyl groups but on the basis of the fatty acid chlorides corresponding to the acyl groups
b) at least one substance $Q^+Cl^-$ in which $Q^+$ is as defined for $Q^+$ in formula (I), in amounts greater than or equal to 1.0% by weight, based on the overall composition,
c) at least one fatty acid salt of the formula (II)

formula (II)

in which
$R^2CO$ is as defined for $R^1$ in formula (I) and
$Q^+$ is as defined for $Q^+$ in formula (I),
in amounts less than or equal to 3.0% by weight, based on the overall composition, and
d) water,
e) and no organic solvents.

2. The composition as claimed in claim 1, which comprises 23.0-27.0% by weight of component a), based on the overall composition.

3. The composition as claimed in claim 1, wherein $Q^+$ is $Na^+$.

4. The composition as claimed in claim 1, which comprises 1.0 to 8.0% by weight of the at least one substance $Q^+Cl^-$, based on the overall composition.

5. The composition as claimed in claim 1, which comprises the at least one fatty acid salt of the formula (II) in amounts of 0.01 to 2.0% by weight, based on the overall composition.

6. The composition as claimed in claim 1, wherein the purity of the acylglycinate of the formula (I) present therein is 90% or greater, this purity being based on the sum total of fatty acid salt of the formula (II) and acylglycinate of the formula (I), and being calculated as purity of the acylglycinates is equal to the amount of acylglycinate divided by (the amount of acylglycinate plus the amount of fatty acid salt).

7. The composition as claimed in claim 1, which has a viscosity of less than 5000 mPa·s at 40° C.

8. A process for production of a cosmetic formulation comprising the step of adding a composition as claimed in claim 1 to the cosmetic formulation.

9. A surfactant in a cosmetic formulation comprising at least one composition as claimed in claim 1.

* * * * *